United States Patent [19]

Gross et al.

[11] Patent Number: 5,156,591
[45] Date of Patent: Oct. 20, 1992

[54] SKIN ELECTRODE CONSTRUCTION AND TRANSDERMAL DRUG DELIVERY DEVICE UTILIZING SAME

[75] Inventors: Joseph Gross, Moshav Mazor; Shlomo Zucker, Yavne, both of Israel

[73] Assignee: S. I. Scientific Innovations Ltd., Petach Tikva, Israel

[21] Appl. No.: 627,104

[22] Filed: Dec. 13, 1990

[51] Int. Cl.⁵ .................................................. A61N 1/30
[52] U.S. Cl. ........................................ 604/20; 128/803
[58] Field of Search .................. 604/20, 290; 128/798, 128/802, 803

[56] References Cited

U.S. PATENT DOCUMENTS

| | | | |
|---|---|---|---|
| H516 | 9/1988 | Lattin et al. | 604/20 |
| 4,640,689 | 2/1987 | Sibalis | 604/20 |
| 4,693,711 | 9/1987 | Bremer et al. | 604/290 |
| 4,708,716 | 11/1987 | Sibalis | 604/20 |
| 4,752,285 | 6/1988 | Petelenz et al. | 604/20 |
| 4,886,514 | 12/1989 | Maget | 604/20 |
| 5,057,072 | 10/1991 | Phipps | 128/798 |

FOREIGN PATENT DOCUMENTS

| | | |
|---|---|---|
| 0096731 | 12/1983 | European Pat. Off. . |
| 0269246 | 1/1988 | European Pat. Off. . |
| 0259013 | 9/1988 | European Pat. Off. . |
| 0299631 | 1/1989 | European Pat. Off. ............. 604/20 |

*Primary Examiner*—Lee S. Cohen
*Assistant Examiner*—J. R. Jastrzab
*Attorney, Agent, or Firm*—Benjamin J. Barish

[57] ABSTRACT

A transdermal drug delivery device includes an electrode, a porous insulating layer on one side of the electrode and impregnated with a liquid containing the drug to be delivered, a reservoir for the liquid on the other side of the electrode, and a displaceable diaphragm controlling the feeding of the liquid from the reservoir to the porous insulating layer via a passageway through the electrode.

18 Claims, 3 Drawing Sheets

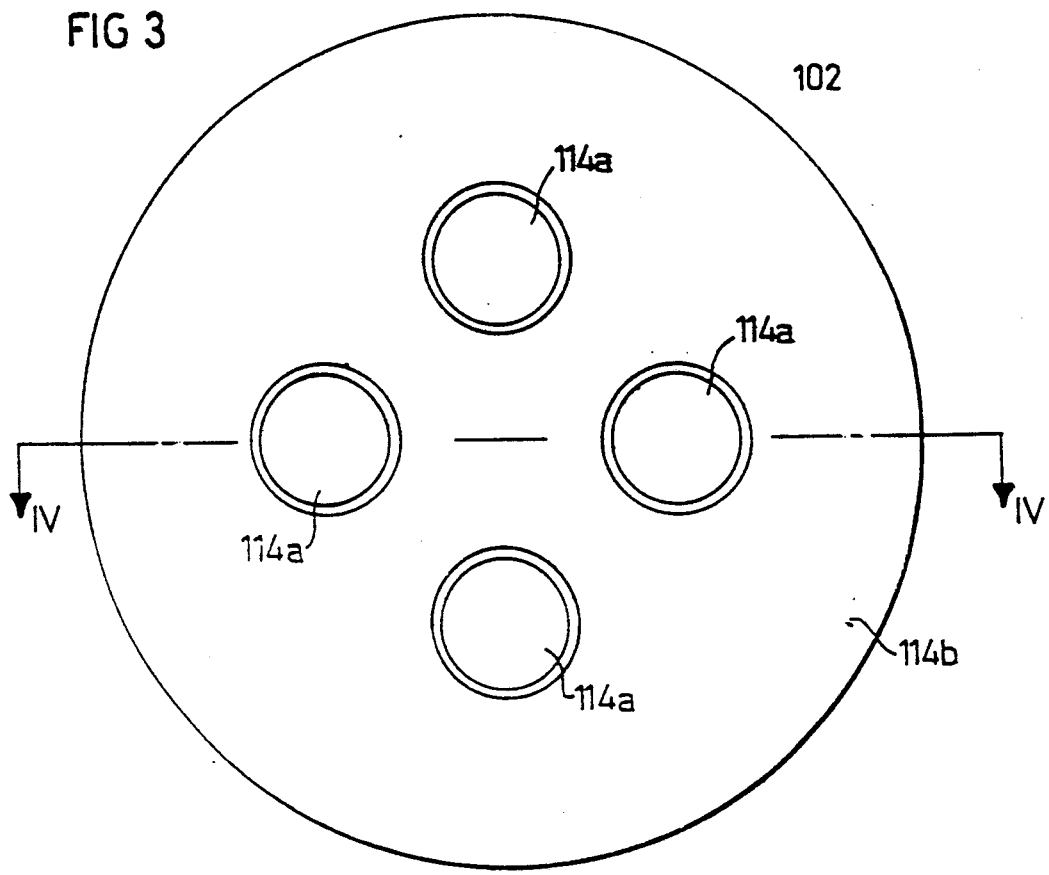
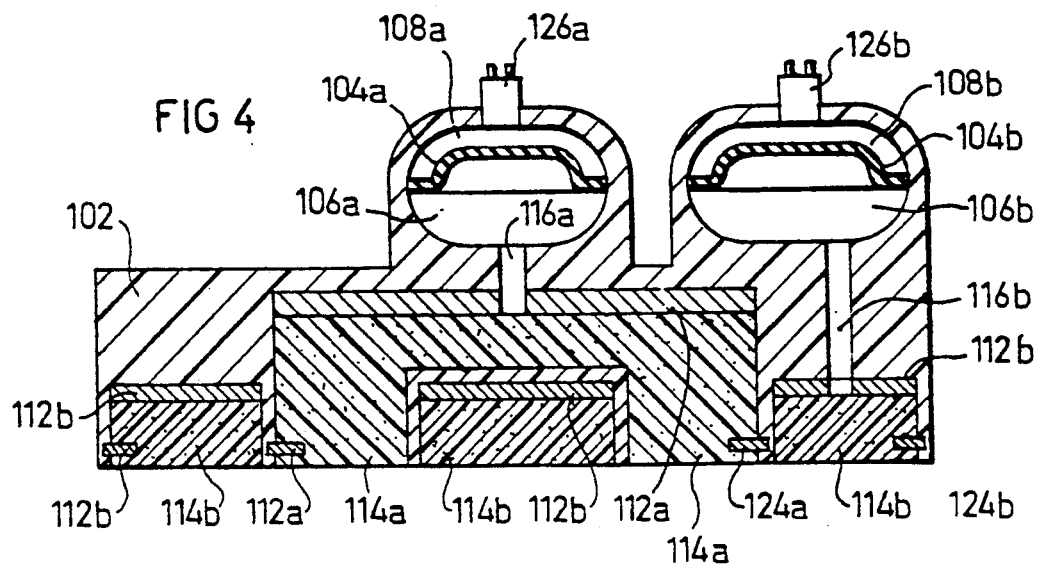

SKIN ELECTRODE CONSTRUCTION AND TRANSDERMAL DRUG DELIVERY DEVICE UTILIZING SAME

FIELD AND BACKGROUND OF THE INVENTION

The present invention relates to a skin electrode construction, and also to a transdermal drug delivery device including such a construction. The invention is particularly applicable to skin electrode constructions for delivering drugs by iontophoresis, and is therefore described below with respect to this application.

Iontophoresis is the process of moving ions into surface tissues with the aid of an electric current. Although this process has long been known, its use for the transdermal delivery of a drug has only recently become of great interest, and many such devices are described in the literature. However, one of the serious limitations in the use of this technique, particularly for delivering drugs at an optimum rate, is the tendency of the device to irritate or burn the recipient's skin because of the heat generated by the iontophoresis electrodes.

Tapper U.S. Pat. No. 4,164,226 discloses an electrode structure to provide protection against skin burns, particularly during transdermal drug delivery by iontophoresis, by covering the face of the skin electrode, normally to be in contact with the subject's skin, with a felt-like material, preferably moistened by a liquid. However, such a device is of very limited application since it cannot be rejuvenated nor can its moisture content be controlled.

OBJECTS AND BRIEF SUMMARY OF THE INVENTION

An object of the present invention is to provide an electrical device of the foregoing type, and particularly a transdermal drug delivery device, having advantages in the above respects.

According to one aspect of the present invention, there is provided an electrical device for application to a subject's skin, including a skin electrode and a porous insulating layer thereover impregnated with a liquid to be placed in contact with the subject's skin in order to reduce or eliminate skin irritation or skin burn; characterized in that the device includes a reservoir for the liquid in communication with the porous insulating layer; a displaceable member controlling the feeding of the liquid from the reservoir to the porous insulating layer; and control means for controlling the displaceable member and thereby the rate of feeding of the liquid from the reservoir to the porous insulating layer.

According to further features in several preferred embodiments of the invention described below, the displaceable member is a diaphragm, and the control means includes a pressure chamber controlling the displacement of the diaphragm.

According to still further features in the described preferred embodiments, the pressure chamber includes an electrolytic cell capable of generating a gas corresponding to the electric current applied to the electrolytic cell. The porous insulating layer also includes a sensor sensing the liquid content of that layer, and the control means includes a control circuit controlled by the sensor for controlling the electric current applied to the electrolytic cell in accordance with the sensed liquid content of the porous insulating layer.

While a device constructed in accordance with the foregoing features may advantageously be used in many applications in order to reduce or eliminate skin irritation or skin burn when an electrode is applied to a subject's skin, the invention is particularly useful in the transdermal delivery of a drug to a subject.

According to another aspect of the present invention, therefore, there is provided a transdermal drug delivery device for delivering a liquid drug to a subject, comprising: a porous insulating layer having means for attaching the device to a subject with one side of the porous insulating layer in contact with the subject's skin; a reservoir for the liquid drug to be delivered on the opposite side of the porous insulating layer; a displaceable member controlling the feeding of the liquid drug from the reservoir to the porous insulating body; and control means for controlling the displaceable member and thereby the rate of feed of the liquid from the reservoir to the porous insulating layer.

In the preferred embodiments of the invention described below, wherein the displaceable member is a diaphragm and the pressure chamber includes an electrolytic cell as briefly described above, the device further includes an electrode interposed between the porous insulating layer and the reservoir for controlling the delivery of the drug by iontophoresis. It will be appreciated, however, that the invention could also be used in a passive-type transdermal drug delivery device not including iontophoresis electrodes.

As will be more apparent from the description below, an electrical device, and particularly a transdermal drug delivery device, constructed in accordance with the foregoing features is capable of delivering a drug (or more than one drug) at a relatively high rate with a minimum of skin irritation or skin burn. A further advantage of the invention is that the drug need not be in gel form, as in previous devices, but could be in liquid form, which inherently provides better migration of the drug to and into the skin.

Further features and advantages of the invention will be apparent from the description below.

BRIEF DESCRIPTION OF THE DRAWINGS

The invention is herein described, by way of example only, with reference to the accompanying drawings, wherein:

FIG. 3 is a bottom plan view of a second form of transdermal drug delivery device constructed in accordance with the present invention;

FIG. 4 is a longitudinal sectional view along lines IV—IV of FIG. 3; and

DESCRIPTION OF PREFERRED EMBODIMENTS

Figure 1:
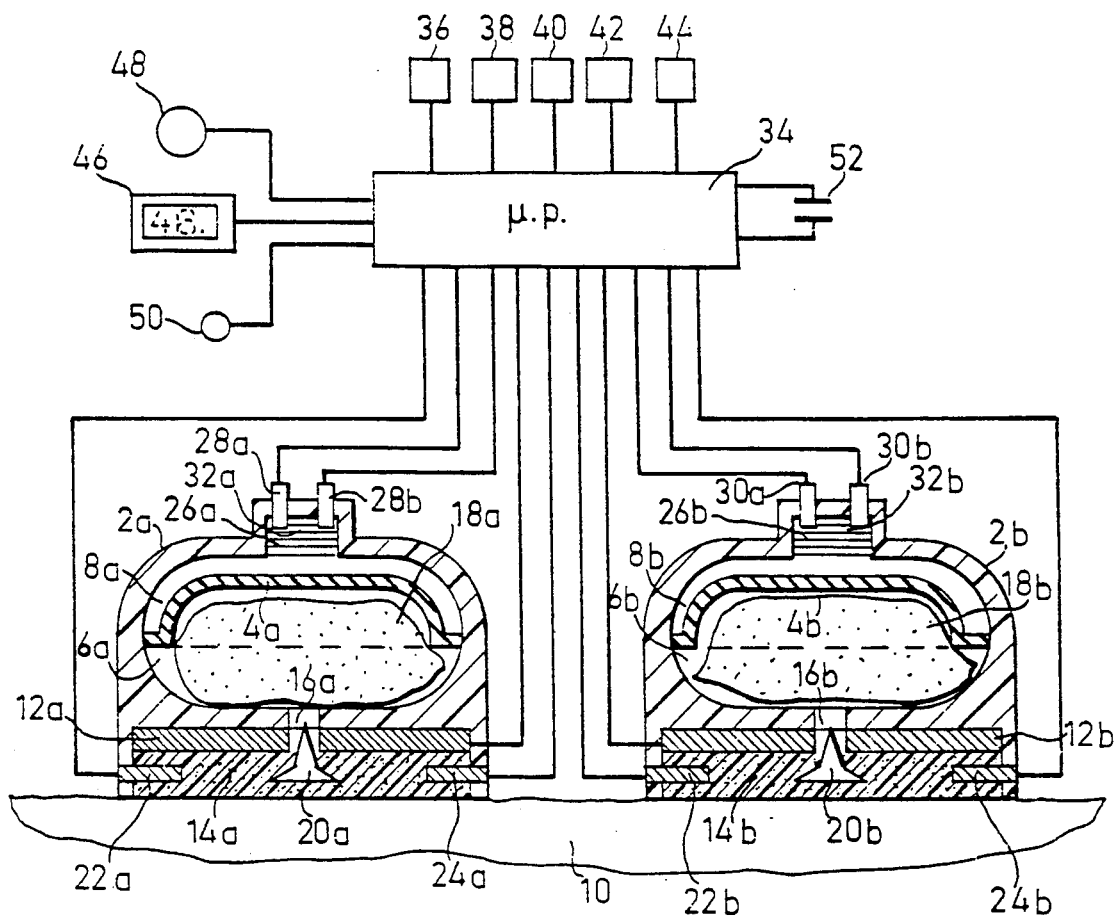
FIG. 1 is a diagrammatic view illustrating one form of transdermal drug delivery device constructed in accordance with the present invention.
Figure 2:
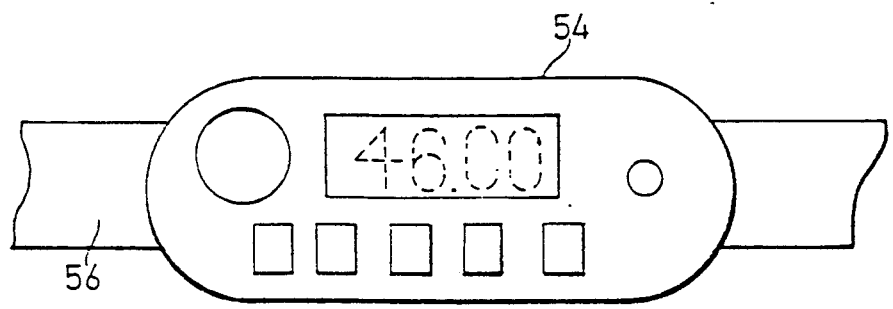
FIG. 2 is a top plan view illustrating the device of FIG. 1 as mounted on a band for application to an arm or leg of the subject.

The Embodiment of FIGS. 1 and 2

FIGS. 1 and 2 illustrate a transdermal drug delivery device which may be used for administering one drug, or two drugs simultaneously, to a person by iontophoresis. It includes two housings 2a, 2b each including an internal compartment containing a deformable diaphragm 4a, 4b dividing the compartment into two expansible-contractible chambers 6a, 6b on one side of the diaphragm, and chambers 8a, 8b on the opposite side. Chambers 6a, 6b serve as liquid reservoirs to contain a liquid, one or both of which may include a drug, to be administered via the subject's skin 10. Chambers 8a, 8b on the opposite side of the diaphragms serve as pressure chambers for controlling the rate of delivery of the liquid in chambers 6a, 6b, as will be described more particularly below.

Each of the housings 2a, 2b further carries a skin electrode 12a, 12b, each covered on its opposite side by a porous insulating layer 14a, 14b which directly contacts the subject's skin. The porous insulating layers 14a, 14b may be of natural or synthetic fibers, such as viscose rayon, polyester fibers, felt, etc.; alternatively, they may be of a cellular plastic material having open interconnecting cells so as to permit permeation therethrough of the liquid within their respective reservoir 6a, 6b.

Each of the housings 2a, 2b further includes a passageway 16a, 16b leading from its liquid reservoir 6a, 6b through its electrode 12a, 12b to its respective porous insulating layer 14a, 14b. The liquid within each reservoir 6a, 6b is normally contained within a plastic bag 18a, 18b. Each bag may be pierced by a piercing element 20a, 20b having a head embedded in the porous insulating layer 14a, 14b of the respective housing, and a pointed tip disposed within the passageway 16a, 16b. Thus pressing the center of a porous insulating layer inwardly will cause its piercing element to pierce its plastic bag 18a, 18b, and thereby permit the liquid within the respective reservoir 6a, 6b to flow via passageway 16a, 16b to the porous insulating layer 14a, 14b of the respective housing.

The skin electrodes 12a, 12b constitute iontophoresis electrodes for controlling the movement of the liquid from the respective porous insulating layer 14a, 14b to and through the subject's skin 10. Thus, electrode 12a in housing 2a may be the cathode, and electrode 12b in housing 2b may be the anode. As known, the rate of delivery of the liquids within reservoirs 6a, 6b from the porous insulating layers 14a, 14b to and through the subject's skin 10 can be controlled by the voltage applied to the two electrodes 12a, 12b.

The porous insulating layers 14a, 14b include sensor electrodes 22a, 22b on one side, and sensor electrodes 24a, 24b on the opposite side, of the respective porous insulating layer. The sensor electrodes are used for sensing the liquid content of the respective porous insulating layer and for controlling the voltage applied to the electrodes 12a, 12b, in response to the sensed liquid content.

Each of the pressure chambers 8a, 8b within the housings 2a, 2b includes an electrolytic cell 26a, 26b. Each electrolytic cell contains a pair of spaced electrodes 28a, 28b and 30a, 30b, separated by an electrolyte 32a, 32b of the type capable of generating a gas (e.g., oxygen, hydrogen or carbon dioxide) when an electric current is applied. Many electrolytes are known for this purpose.

The illustrated device further includes a microprocessor 34 connected to all of the above-named electrodes, namely: the skin or iontophoresis electrodes 12a, 12b; the liquid-content sensor electrodes 22a, 22b and 24a, 24b; and the electrolytic cell electrodes 28a, 28b and 30a, 30b. Microprocessor 34 has a number of inputs, as follows: a Stop-Start input 36, a Select Rate input 38, a Select Mode input 40, a Set Minutes input 42, and a Set Hours input 44. These inputs permit the microprocessor 34 to be preprogrammed to deliver the liquids within reservoirs 6a, 6b at preselected rates and times.

Microprocessor 34 includes the following additional outputs: a visual display output 46, e.g., an LCD (liquid crystal display) for displaying the preselected rate and/or time; an audio alarm 48 (e.g., a buzzer), which is energized under certain prescribed conditions (e.g., if the drug delivery rate increases above a predetermined maximum, or drops below a predetermined minimum); and a visual signal 50, e.g., an LED (light emitting diode) which is energized when a prescribed condition occurs.

The device is powered by a self-contained battery 52. The two housings 2a, 2b, together with the microprocessor 34 and the other described components, may all be included in a common housing 54 (FIG. 2) carried by a band 56 permitting the device to be conveniently applied to an arm or leg of the subject.

The device illustrated in FIGS. 1 and 2 is used in the following manner:

If a single drug is to be administered to the subject, the drug is included in liquid form in one of the reservoirs 6a, 6b, whereas the other reservoir is filled with a liquid (e.g., water) used merely for moistening the respective porous insulating layer. However, if two drugs are to be administered simultaneously, then each reservoir 6a, 6b includes a drug in liquid form. The liquids in the two reservoirs 6a, 6b are preferably in plastic bags, so that the reservoirs can be conveniently refilled.

When the device is to be used for administering one or more drugs to the subject, the central region of each of the two porous insulating layers 14a, 14b is pressed inwardly to cause its piercing elements 20a, 20b to pierce the plastic bag in its respective reservoir 6a, 6b, and thereby to permit the liquid to flow via its passageway 16a, 16b to its respective porous insulating layer.

The rate of delivery of the liquids in reservoirs 6a, 6b is controlled both by the current supplied to the iontophoresis or skin electrodes 12a, 12b, and also by the current supplied to the electrolytic-cell electrodes 28a, 28b and 30a, 30b in the respective housing 2a, 2b. Thus, the supply of current to the electrolytic cell electrodes 28a, 28b and 30a, 30b causes the electrolyte in the respective cell to generate a gas which increases the pressure within the pressure chambers 8a, 8b, thereby expanding those chambers and contracting the liquid-containing reservoirs 6a, 6b; this increases the rate of flow of the liquid via their respective passageways 16a, 16b to their porous insulating layers 14a, 14b. On the other hand, the supply of electric current to the skin electrodes 12a, 12b controls the migration, by iontophoresis, of the liquid from the porous insulating layers 14a, 14b to and through the subject's skin. The liquid content of the porous insulating layers 14a, 16a is continuously monitored by the sensor electrodes 22a, 22b and 24a, 24b, to automatically control microprocessor 34.

The Embodiment of FIGS. 3 and 4

FIGS. 3 and 4 illustrate another form of transdermal drug delivery device also operating by iontophoresis. This device includes a single housing 102 formed with two compartments each divided by a deformable diaphragm 104a, 104b to define a liquid-containing reservoir 106a, 106b and a pressure chamber 108a, 108b. The device further includes two electrolytic cells 126a, 126b adapted to generate a gas for increasing the pressure in the pressure chambers 108a, 108b, and thereby for controlling the rate of delivery of the liquid in the reservoirs 106a, 106b. In the device of FIGS. 3 and 4, however, the liquid (e.g., including a drug) in reservoir 106a is fed via a passageway 116a through one of the electrodes 112a to a plurality of sections of one porous insulating layer 114a arranged in a circular array around the center of housing 102, whereas the liquid in chamber 106b (which may also include a drug or merely a moisturizer) is fed via passageway 116b through its electrode 112b to its porous insulating layer 114b disposed in the spaces between and around the porous insulating layer 114a. Porous insulating layer 114a feeding the drug is also provided with sensor electrodes 122a, 124a, in order to sense the liquid content of that layer; and porous insulating layer 114b is similarly provided with sensor electrodes 122b, 124b for sensing the liquid content of that layer.

The device illustrated in FIGS. 3 and 4 is otherwise constructed in the same manner as described above with respect to FIGS. 1 and 2, operates in substantially the same manner, and provides substantially the same advantages, except that it has the capacity of delivering the drug (or drugs) at higher rates.

Figure 5:
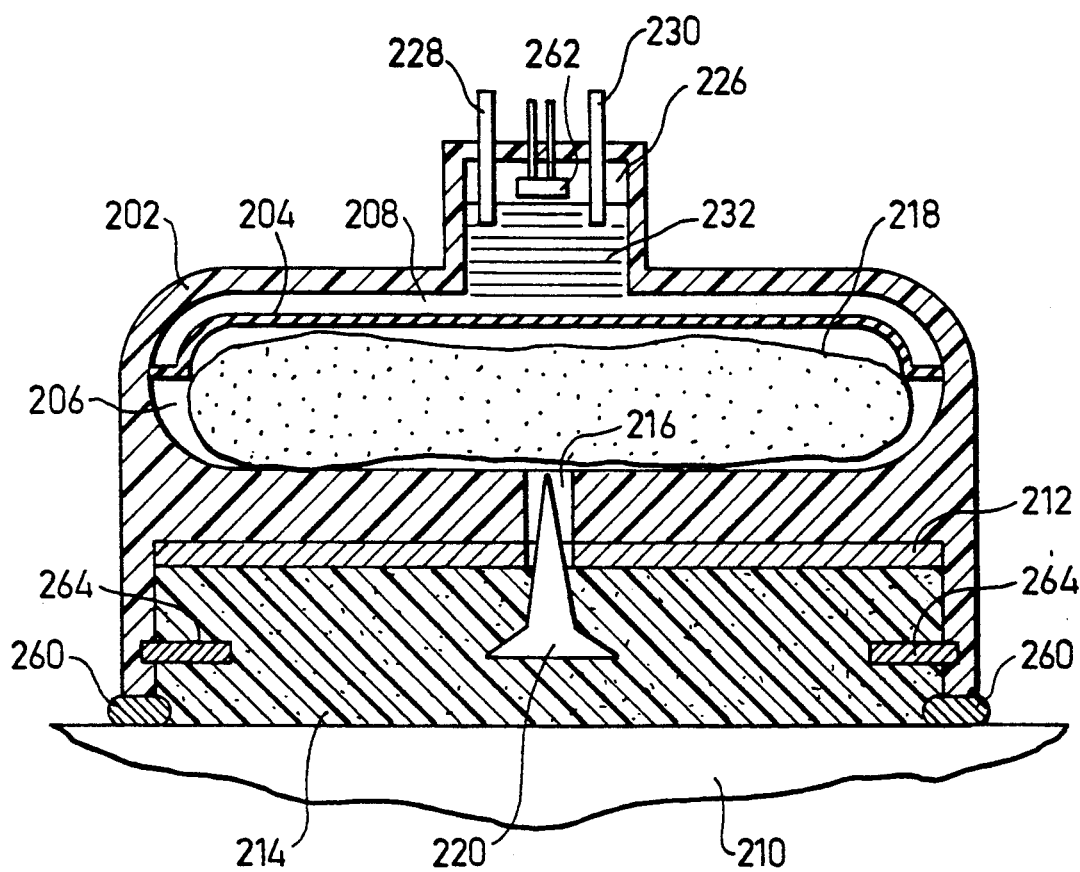
FIG. 5 is a longitudinal sectional view illustrating a third form of transdermal drug delivery device constructed in accordance with the present invention.

The Device of FIG. 5

The device illustrated in FIG. 5 is very similar to the construction described above with respect to FIGS. 1 and 2. In FIG. 5, however, the construction for only one of the skin (iontophoresis) electrodes, therein designated 212, is illustrated. Thus, when the device is to include two such electrodes, both may be constructed as illustrated in FIG. 5.

The device illustrated in FIG. 5 includes a housing 202 formed with an internal compartment including a deformable diaphragm 204 dividing the interior of the compartment into a liquid-containing reservoir 206 and a pressure chamber 208. The device is to be applied to the skin 210 of the subject, and further includes a skin electrode 212, a porous insulating layer 214 to contact the skin, and a passageway 216 for feeding the liquid from chamber 206 via electrode 212 to the porous insulating layer 214 when the bag 218 containing the liquid is pierced by a piercing element 220. The device further includes an electrolytic cell 226 containing a pair of electrodes 228, 230 and an electrolyte 232 capable, when electric current is applied, of generating a gas to increase the pressure in chamber 208, and thereby to control the rate of feeding of the liquid therefrom to the porous insulating layer 214, and from there to the subject's skin 210.

Insofar as described above, the device of FIG. 5 is constructed and operates in the same manner as the device of FIGS. 1 and 2.

The device of FIG. 5, however, further includes a sealing ring 260 circumscribing the porous insulating body 214. Thus, when the device is applied to the subject's skin, sealing ring 260 seals the housing 202 with respect to the subject's skin, such that the pressure, which builds up in pressure chamber 208 by the generation of gas from the electrolytic cell 226, is also applied directly to the subject's skin via the porous insulating layer 214. The pressure thus applied to the skin is sensed by a pressure sensor 262 within the electrolytic cell 226, and can be used for controlling the microprocessor.(34, FIG. 1), to maintain the appropriate pressure for the desired rate of delivery of the drug to the subject. The liquid content of the porous insulating layer is sensed by sensor electrodes 264.

When the invention is embodied in a transdermal drug delivery device for delivering a drug by iontophoresis, it can be shown that the drug delivery rate (D) is dependent on the following relationship:

$$D = \frac{P_e A(P_c - P_{AB})}{d \cdot P_{AB}} + kI$$

wherein:
$P_e$ = permeability of the skin
$d$ = skin thickness
$k$ = iontophretic delivery constant
$I$ = electrical current
$P$ = pressure in the respective pressure chamber
$P^c$ = absolute pressure (ambient)
$A^{AB}$ = active skin area Thus, in the conventional iontophoresis process, the delivery rate is determined by the "kI" factor in the above equation; but in the present invention wherein a pressure is applied by the electrolytic cell, the delivery rate may be increased by the first ("pressure") factor in the above equation. The liquid content of each porous insulating layer is continuously monitored by the sensor electrodes to maintain the desired concentration of liquid therein, thereby minimizing or eliminating skin irritation or skin burn.

It will also be appreciated that the invention could be embodied in a "passive patch", i.e. without the iontophoresis electrodes, whereupon the delivery would be determined by the first ("pressure") factor in the above equation.

It will be appreciated that the devices illustrated in FIGS. 1, 2, and 3, 4 may also include the features described above with respect to FIG. 5, namely the sealing ring 260 for sealing the housing with respect to the subject's skin, and the pressure sensor 262 for sensing the pressure. Many other variations, modifications and applications of the invention will be apparent.

What is claimed is:

1. An electrical device for application to a subject's skin, including an electrode and a porous insulating layer thereover impregnated with a liquid to be placed in contact with the subject's skin in order to reduce or eliminate skin irritation or skin burn; characterized in that said device includes:
   a reservoir for said liquid in communication with said porous insulating layer;
   a displaceable member controlling the feeding of said liquid from the reservoir to said porous insulating layer;
   and control means for controlling said displaceable member and thereby the feeding of the liquid from the reservoir to said porous insulating layer so as to reduce or eliminate skin irritation or skin burn.

2. The device according to claim 1, wherein said displaceable member is a diaphragm, and said control means includes a pressure chamber and means for controlling the pressure in said chamber for controlling the displacement of said diaphragm.

3. The device according to claim 2, wherein said pressure chamber includes an electrolytic cell capable of generating a gas corresponding to the electric current applied to the electrolytic cell.

4. The device according to claim 3, wherein said porous insulating layer includes a sensor sensing the liquid content of the porous insulating layer, and said control means includes a control circuit controlled by said sensor for controlling the electric current applied to said electrolytic cell in response to the sensed liquid content of the porous insulating layer.

5. The device according to claim 1, wherein said porous insulating layer is circumscribed by a sealing ring to be contacted by the subject's skin.

6. The device according to claim 5, wherein said pressure chamber further includes a pressure sensor sensing the pressure therein and controlling said control means in response thereto.

7. The device according to claim 1, wherein said reservoir is configured to receive a bag of the liquid on one side of the porous insulating layer, said device further including a piercing element for piercing the bag when the device is to be used for transdermal delivery of the liquid.

8. The device according to claim 1, further including a second electrode and a voltage source connected to the electrodes for controlling the delivery of a drug by iontophoresis.

9. The device according to claim 1, wherein there are a pair of said porous insulating layers, each including an electrode, a reservoir, and a displaceable diaphragm for controlling the feed of the liquid from each reservoir via its respective electrode to its respective porous insulating layer.

10. A transdermal drug delivery device for delivering a liquid drug to a subject, comprising:
    a porous insulating layer having means for attaching the device to a subject with one side of the porous insulating layer in contact with the subject's skin;
    a reservoir on an opposite side of the porous insulating layer for a liquid drug to be delivered;
    a displaceable diaphragm controlling the feeding of the liquid drug from the reservoir to the porous insulating layer;
    and control means including a pressure chamber having an electrolytic cell capable of generating a gas corresponding to electric current applied to the electrolytic cell for controlling said displaceable member and thereby the rate of feed of the liquid from the reservoir to said porous insulating layer.

11. The device according to claim 10, wherein said porous insulating layer includes a sensor sensing the liquid content thereof, and said control means further includes a control circuit controlled by said sensor for controlling the electric current applied to said electrolytic cell in response to said sensed liquid content of porous insulating layer.

12. A transdermal drug delivery device, for delivering a drug to a subject, comprising:
    first and second electrodes each covered on one side by a porous insulating layer impregnated with a liquid to be placed in contact with the subject's skin;
    a reservoir for each liquid on the other side of each electrode in communication with the porous insulating layer thereof, at least one liquid including a drug to be transdermally delivered to the subject;
    each of said reservoirs including a displaceable member controlling the feed of the liquid from its respective reservoir to the porous insulating layer of its respective electrode;
    and control means for controlling said displaceable members, and thereby the rate of feed of the liquid, from each reservoir to the porous insulating layer of its respective electrode.

13. The device according to claim 12, wherein each of said displaceable members is a diaphragm, and said control means includes a pressure chamber for each diaphragm controlling the displacement thereof.

14. The device according to claim 13, wherein each of said pressure chambers includes an electrolytic cell capable of generating a gas corresponding to the electric current applied to the electrolytic cell.

15. The device according to claim 14, wherein each of said porous insulating layers includes a sensor sensing the liquid content of the respective porous insulating layer, said control means including a control circuit controlled by each of said sensors for controlling the electric current applied to the electrolytic cell of its respective electrode automatically in response to the sensed liquid content of the respective porous insulating layer.

16. The device according to claim 15, wherein both of said electrodes, porous insulating layers, and diaphragms, are carried by a band adapted to be applied to the arm or leg of the subject.

17. The device according to claim 12, wherein both of said electrodes, their porous insulating layers, and their reservoirs, are disposed in side-by-side relation.

18. The device according to claim 12, wherein there are a plurality of sections of said first electrode covered by sections of said porous insulating layer in spaced relation with respect to each other, said second electrode and its porous insulating layer occupying spaces between said sections of the first electrode.

* * * * *